(12) United States Patent
Zhang et al.

(10) Patent No.: US 8,927,690 B2
(45) Date of Patent: *Jan. 6, 2015

(54) PROCESS FOR PURIFYING CYCLOLIPOPEPTIDE COMPOUNDS OR THE SALTS THEREOF

(75) Inventors: Zhaoli Zhang, Shanghai (CN); Shidong Liu, Shanghai (CN); Zhonghao Zhuo, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 75 days.

This patent is subject to a terminal disclaimer.

(21) Appl. No.: 13/877,427

(22) PCT Filed: Sep. 27, 2011

(86) PCT No.: PCT/CN2011/080220
§ 371 (c)(1),
(2), (4) Date: Jul. 11, 2013

(87) PCT Pub. No.: WO2012/041218
PCT Pub. Date: Apr. 5, 2012

(65) Prior Publication Data
US 2013/0281665 A1     Oct. 24, 2013

(30) Foreign Application Priority Data
Sep. 29, 2010 (CN) .......................... 2010 1 0297406

(51) Int. Cl.
| A61K 38/00 | (2006.01) |
| C07K 1/00 | (2006.01) |
| C07K 1/22 | (2006.01) |
| C07K 7/56 | (2006.01) |

(52) U.S. Cl.
CPC .... C07K 1/22 (2013.01); C07K 7/56 (2013.01)
USPC ..................................................... 530/344

(58) Field of Classification Search
None
See application file for complete search history.

(56) References Cited

U.S. PATENT DOCUMENTS

| 4,874,843 A | 10/1989 | Baker |
| 5,376,634 A | 12/1994 | Iwamoto et al. |
| 2010/0249371 A1 | 9/2010 | Gurnani et al. |

FOREIGN PATENT DOCUMENTS

| EP | 0431350 A1 * | 6/1991 |
| EP | 0486011 A2 | 5/1992 |
| EP | 0933422 A1 * | 8/1999 |
| EP | 1197557 A1 | 4/2002 |
| EP | 1137663 B1 | 8/2006 |
| WO | WO 2012/041218 A1 | 4/2012 |

OTHER PUBLICATIONS

Kanasaki et al. "FR209602 and Related Compounds, Novel Antifungal Lipopeptides from Coleophoma crateriformis No. 738". J. Antibiotics 59:137-144. Published 2006.*

Fujie A "Discovery of micafungin (FK463): A novel antifungal drug derived from a natural product lead". Pure Applied Chemistry 79:603-614. Published 2007.*

International Search Report and Written Opinion dated Jan. 5, 2012 issued in PCT/CN2011/080220 (WO/2012/041218)[with English Translation].

* cited by examiner

Primary Examiner — Maury Audet
Assistant Examiner — Zachary J Miknis
(74) Attorney, Agent, or Firm — Tom Hunter; Weaver Austin Villeneuve & Sampson LLP

(57) ABSTRACT

A process for purifying cyclic lipopeptide compounds or salts thereof comprising the steps of: (1) charging a crude compound of Formula I onto a macroporous adsorption resin; (2) washing the macroporous adsorption resin using water, an organic solvent or a mixed solution of an organic solvent and water as a washing liquid; and (3) eluting the compound of Formula I from the macroporous adsorption resin using water, an organic solvent or a mixed solution of an organic solvent and water as an eluent. The purification method has the advantages of using a small amount of organic solvents, using no silica gel, and causing little damage to the environment; the purity of the collected compound of formula I is also improved as compared with the methods previously disclosed.

17 Claims, 1 Drawing Sheet

PROCESS FOR PURIFYING CYCLOLIPOPEPTIDE COMPOUNDS OR THE SALTS THEREOF

CROSS-REFERENCE TO RELATED APPLICATIONS

This application is a 371 National Phase of PCT/CN2011/080220, filed on Sep. 27, 2011, which claims benefit of and priority to CN 201010297406.2, filed on Sep. 29, 2010, which is incorporated herein by reference in its entirety for all purposes.

TECHNICAL FIELD

The present invention relates to the field of organic chemistry, particularly, to the process for purifying the cyclolipopeptide compound of Formula I or the salts thereof.

BACKGROUND

Fungal-infections have become the major cause for the high incidence and mortality in immunodeficiency patients. During the past 20 years, the incidence of mycotic infection has increased significantly. The high-risk population for the fungal-infection includes critical patients, surgical patients and the patients with HIV-infection, leukemia as well as other tumors. Additionally, the organ transplant recipients are also the high-risk population for fungal-infection.

The echinocandins are novel anti-fungal medicaments, which are effective in treating *Candida-* or *aspergillus-*infections, and the examples of which are Caspofungin and Micafungin. The echinocandins inhibit the fungi by inhibiting the formation of 1,3-β glucosidic bond, thereby reducing the toxicity toward the human and the side effects, while maintaining high efficiency. Therefore, compared with the traditional antifungal-medicaments, the echinocandins are safer when they are used.

FK463 (Micafungin) is the compound of Formula III, which is obtained by cutting the side-chain of compound FR901379 of Formula II ($M_0$), thus forming compound FR179642 ($M_1$) of Formula I, and adding the side-chain to compound of Formula I by synthesis. Therefore, the compound of Formula I with high-purity is very important for obtaining Micafungin with high-purity.

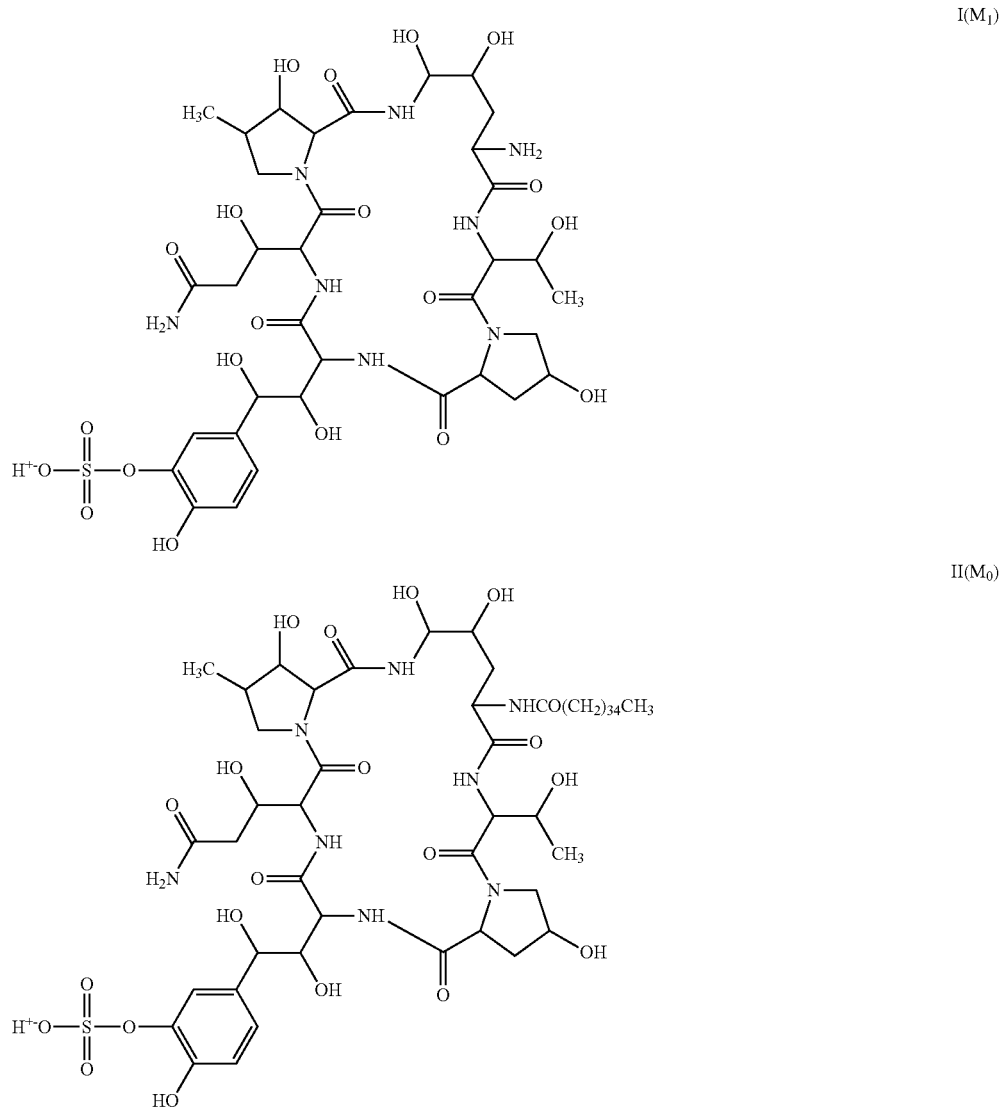

-continued

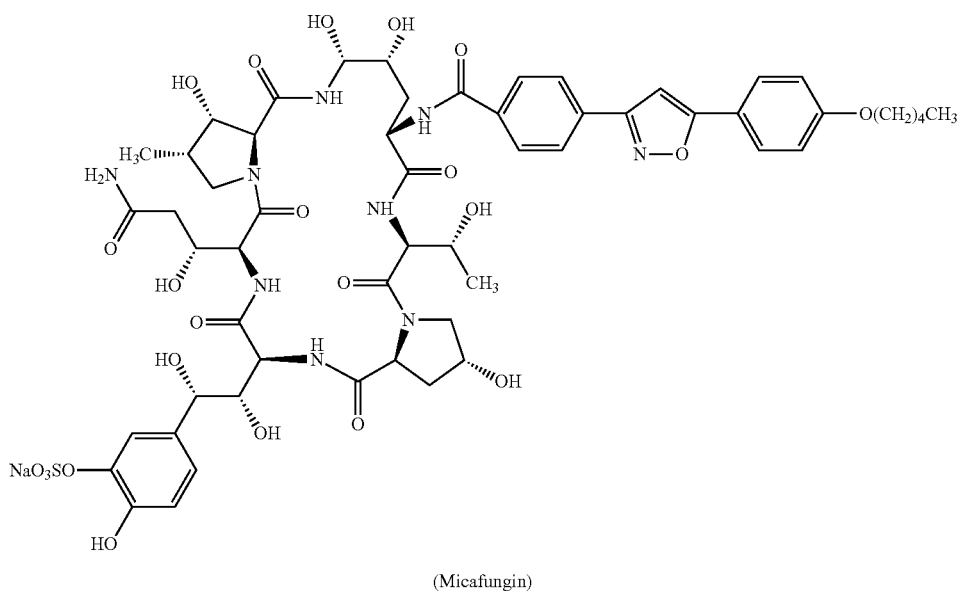

(Micafungin)

The following strains have been reported for transforming the compound of Formula II into the compound of Formula I by deacylating the acyl side-chain of the former compound: Streptomyces, such as Streptomyces anulatus No. 4811, Streptomyces anulatus No. 8703, Streptomyces sp. No. 6907, and IFO13244, IFO6798, IFO31963, IFO9951, NRRL12052, etc. U.S. Pat. No. 5,376,634 has disclosed a method for purifying the compound of Formula I, wherein, the method comprises the following steps: the compound of Formula II is transformed into the compound of Formula I by enzyme reaction, the transforming liquid is filtered, the compound of Formula I is purified through active coal column and silica gel column in turn, and upon concentration under reduced pressure, the compound of Formula I is obtained in white solid. For this method, the amount of the used organic solvent is great, and the used active coal and silica gel can not be recycled, therefore, such method will pollute the environment, be harmful to the physical healthy of the operators, and not suitable for large-scale production.

Therefore, it is urgent in the art to find a purification method without using great amount of solvent or silica gel, and such method can not only overcome the defects in the prior art, but improve the purity of the compound of Formula I.

SUMMARY OF THE INVENTION

The subject of the present invention is to provide a process for purifying the compound of Formula I.

In the present invention, a process for purifying the compound of Formula I or the salts thereof is provided, said process comprising the following steps:

(1) loading the crude compound of Formula I onto a macroporous adsorption resin;

(2) washing the macroporous adsorption resin using water, an organic solvent or a mixed solution of an organic solvent and water as the washing liquid; and (3) eluting the compound of Formula I from the macroporous adsorption resin using water, an organic solvent or a mixed solution of an organic solvent and water as eluent.

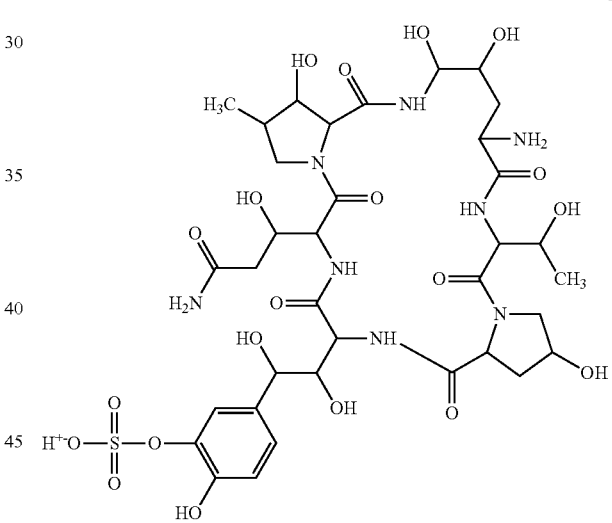

In the above purification process provided by the invention, the macroporous adsorption resin is selected from a non-polar aromatic adsorption resin polymerized from styrene and divinylbenzene, or a methacrylic adsorption resin of moderate polarity with methacrylate units in its structure.

In another preferred embodiment, the adsorption resin is selected from: XAD-1, XAD-2, XAD-3, XAD-4, XAD-5, XAD-16, XAD-16HP, HP-10, HP-20, HP-20ss, HP-21, HP-30, HP-40, HP-50, SP-825, SP-850, SP-70, SP-700, SP-207, XAD-6, XAD-7, XAD-7HP, XAD-8, HP-2MG, or the mixture thereof.

In another preferred embodiment, the adsorption resin comprises halogen and is bonded with styrene polymer matrix through chemistry bond.

In another preferred embodiment, the adsorption resin comprises bromine and is bonded with styrene polymer matrix through chemistry bond.

In another preferred embodiment, the adsorption resin is selected from: SP-207, SP-207ss, or the mixture thereof.

In another preferred embodiment, in step (1), the solution comprising the crude compound of Formula I is allowed to flow through the chromatographic column filled with the macroporous adsorption resin or the solution comprising the crude compound of Formula I is mixed with the macroporous adsorption resin, thereby loading the crude compound of Formula I onto the macroporous adsorption resin; and the flow rate is 0.1-10 column volumes per hour.

In another preferred embodiment, the solution comprising the crude compound of Formula I comprises ionizable salts. The macroporous adsorption resin is selected from a non-polar aromatic adsorption resin polymerized from styrene and divinylbenzene, or a methacrylic adsorption resin of moderate polarity with methacrylate units in its structure. The ionizable salt is selected from sulfates, nitrates, salts comprising halogen, phosphates, acetates, carbonates, citrates, silicates, persulfates, chromates, lactates, oxalates, etc., or the mixture thereof.

In the above purification process provided by the invention, in step (2), the volume percentage of the organic solvent is 0-3%, preferably 0-2%, based on the total volume of the washing liquid.

In the above purification process provided by the invention, in step (3), the volume percentage of the organic solvent is 0-20%, preferably 0-5%, based on the total volume of the eluent.

In the above purification process provided by the invention, in step (1), the weight ratio of the crude compound of Formula I to the macroporous adsorption resin is 0.1-15 (g/L); preferably, 5-10 (g/L).

In the above purification process provided by the invention, the organic solvent is selected from: C1-4 alcohol, C1-4 ketone; preferably, the organic solvent is selected from: methanol, ethanol, propanol, butanol, acetone, butanone, or the mixture thereof; most preferably, selected from: methanol, ethanol or acetone.

Accordingly, a purification method without using great amount of solvent and silica gel is provided in the invention, and such method can not only overcome the defects in the prior art, but improve the purity of the compound of Formula I.

DETAILED DESCRIPTION OF THE INVENTION

Figure 1:
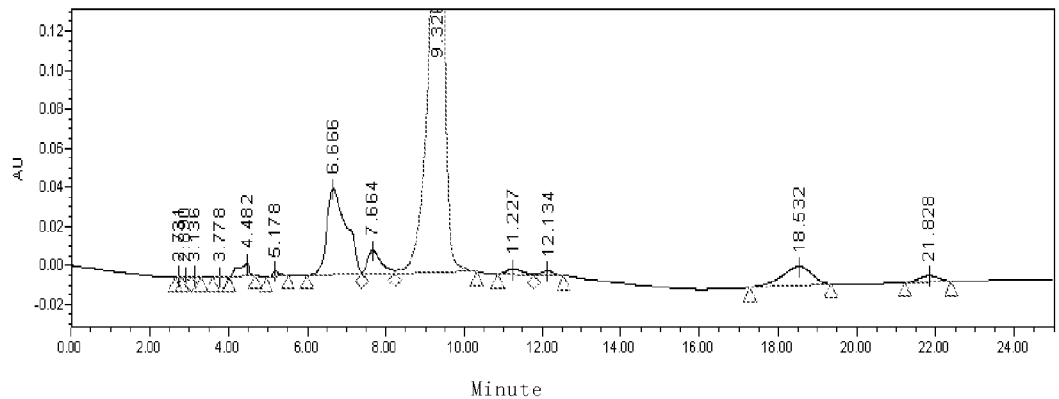
FIG. 1 shows the HPLC chromatogram of the crude compound 1 of Formula I according to Example 1.

Through a great deal of experiments, the inventors have discovered that the aromatic macroporous adsorption resin, especially aromatic derivative resin, such as the aromatic resin with bromine bonded on its skeleton, has improved hydrophobic adsorption, and such resin will exhibit strong adsorption for the substance with strong hydrophilicity, such as the compound of Formula I. The resin is significantly efficient in purifying the compound of Formula I with the relevant impurities. The non-polar aromatic adsorption resin polymerized from styrene and divinylbenzene, or a methacrylic adsorption resin of moderate polarity with methacrylate units in its structure has weak hydrophobic adsorption, therefore, will exhibit weak adsorption for the substance with strong hydrophilicity, such as the compound of Formula I. However, the inventors have surprisingly discovered that when the compound of Formula I is absorbed onto the macroporous adsorption resin, ionizable salts can be added to improve the hydrophobicity of the target compound, therefore, the compound of Formula I can be readily absorbed on the resin, thereby purifying the compound of Formula I.

The process for purifying the compound of Formula I provided by the present invention includes the following steps:

in the first step, loading the crude compound of Formula I onto a macroporous adsorption resin;

in the second step, washing the macroporous adsorption resin by using water, organic solvent or a mixed solution of organic solvent and water as the washing liquid; and in the third step, eluting the compound of Formula I from the macroporous adsorption resin by using water, organic solvent or a mixed solution of an organic solvent and water as eluent.

The first step can be performed by bringing the solution of the crude compound of Formula I into contact with the macroporous adsorption resin. The contact can be performed by: a. directly feeding the adsorption resin into the solution comprising the crude compound of Formula I, and agitating the resulting mixture for 5-120 mins; or b. filling the chromatographic device, such as chromatographic column with the adsorption resin, and the solution comprising the crude compound of Formula I being allowed to flow through the chromatographic column, wherein the flow rate can be 0.1-10 column volumes per hour.

In one example of the invention, the purification process includes the following steps:

A. directly feeding the adsorption resin into the solution comprising the crude compound of Formula I, and agitating the resulting mixture for 5-120 mins;

B. separating the solution comprising the crude compound of Formula I from the resin;

C. washing the macroporous adsorption resin in step B by using water, an organic solvent or a mixed solution of an organic solvent and water as the washing liquid;

D. eluting the washed adsorption resin obtained in step C by using water, an organic solvent or a mixed solution of an organic solvent and water as eluent, and then collecting the eluate comprising the compound of Formula I, thereby obtaining the purified compound of Formula I.

In step B, the separation includes, for example filtration and centrifugation, for separating the resin from filtrate phase.

In all of the purification processes provided by the invention, the organic solvent is selected from: $C_{1-4}$ alcohol, $C_{1-4}$ ketone, or the mixture thereof; preferably, methanol, ethanol, propanol, butanol, acetone, butanone, or the mixture thereof.

In all of the purification processes provided by the invention, the macroporous adsorption resin is selected from a non-polar aromatic adsorption resin polymerized from styrene and divinylbenzene, or a methacrylic adsorption resin of moderate polarity with methacrylate units in its structure.

Preferably, the resin is selected from: XAD series absorption resin (RohmHaas, US), Diaion HP series absorption resin (Mitsubishi Chemical Corporation, JP), and the adsorption resin comprising bromine and bonded with styrene polymer matrix through chemistry bond. More preferably, the resin is selected from: XAD-1, XAD-2, XAD-3, XAD-4, XAD-5, XAD-6, XAD-7, XAD-7HP, XAD-8, XAD-16, XAD-16HP, HP-10, HP-20, HP-20ss, HP-21, HP-30, HP-40, HP-50, HP-2MG, SP-825, SP-850, SP-70, SP-700, SP207, SP207ss, or the mixture thereof. Most preferably, the resin is selected from: HP20, XAD-16, XAD-16HP, SP207, or mini-granulated products, such as HP-20ss, SP207ss, the particle size of which is 0.063 mm-0.150 mm, and the separation performance of which has been greatly improved.

Additionally, the inventors have discovered that the adsorption resin comprising halogen and bonded with styrene polymer matrix through chemistry bond possesses higher absorption and separation efficiency. The adsorption resin comprising bromine and bonded with styrene polymer matrix through chemistry bond is preferred, and the most preferred resin is SP207, SP207ss, or the mixture thereof. Currently, the commercially available adsorption resins comprising halogen and bonded with styrene polymer matrix through chemistry bond are primarily SP207, SP207ss (Mitsubishi Chemical Corporation, JP), but not limited to the two types.

With respect to the absorption resin without halogen, the crude compound of Formula I is mixed with ionizable salts before loading the crude compound of Formula I, for increasing the conductivity of the loading solution and the hydrophobicity of the target compound of Formula I, thereby improving the absorption of the resin for the target compound. The ionizable salt is selected from sulfates, nitrates, salts comprising halogen, phosphates, acetates, carbonates, citrates, silicates, persulfates, chromates, lactates, oxalates, etc., or the mixture thereof. Preferably, the ionizable salt is selected from one or more of the following group consisting of common salts: salts comprising halogen, sulfates, phosphates, acetates, carbonates, and citrates. Most preferably, the resin is selected from: NaCl, KCl and $(NH_4)_2SO_4$.

In the second step of the purification process provided by the invention, the concentration of the organic solvent in the washing liquid is 0-3%; preferably, 0-2%. The ionizable salt can be added into the washing liquid as well. The ionizable salt includes sulfates, nitrates, salts comprising halogen, phosphates, acetates, carbonates, citrates, silicates, persulfates, chromates, lactates, oxalates, etc., or the mixture thereof. Preferably, the ionizable salt is selected from one or more of the following group consisting of common salts: salts comprising halogen, sulfates, phosphates, acetates, carbonates, and citrates. Most preferably, the resin is selected from: NaCl, KCl and $(NH_4)_2SO_4$.

In the third step of the purification process provided by the invention, the concentration of the organic solvent in the eluent is 0-20%; preferably, 0-5%.

In the purification process provided by the invention, washing can be performed for 1, 2, or 3 times. The flow rate for washing can be 0.1-10 column volumes per hour. The flow rate for elution can be 0.1-10 column volumes per hour.

As used herein, "compound of Formula I" and "compound I" can be used interchangeably, both referring to the compound having the following structure or the pharmaceutically acceptable salts thereof:

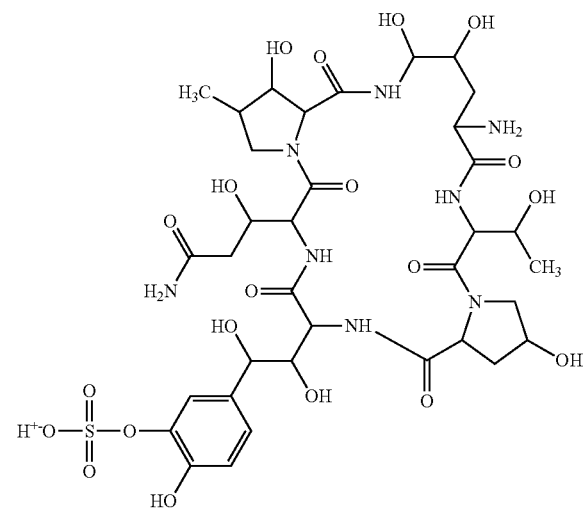

I

As used herein, "pharmaceutically acceptable salt" means salts formed from the following bases: inorganic base, such as sodium, potassium, magnesium, calcium, aluminium, etc.; organic base, such as methylamine, ethylamine, ethanolamine, diethanolamine, triethanolamine, cyclohexanolamine, lysine, ornithine, etc., or other bases relevant to the pharmaceutically acceptable salts.

As used herein, "purity of the compound of Formula I", "purity of compound I" and "HPLC purity of compound I" can be used interchangeably, all referring to the percentage of the peak area of compound I over the sum of all peak areas as measured under the detecting conditions of high performance liquid chromatography (HPLC) provided by the invention.

As used herein, "crude compound of Formula I" and "crude compound I" can be used interchangeably, both referring to a mixture containing <80% of compound I as measured under the detecting conditions of high performance liquid chromatography (HPLC) provided by the invention. Crude compound I can be obtained by using any suitable process known in the art, including for example but not limited to the processes described in Example 1 of EP0431350B1, wherein crude compound I was obtained by fermenting Coleophoma sp. F-11899 (FERM BP2635), and then extracting the mycelia using a organic solvent. Preferably, the extraction is performed by directly adding the fermentation culture into 2 times the volume of the organic solvent. The preferred organic solvent is selected from methanol, ethanol or acetone.

As used herein, "solution comprising crude compound of Formula I" and "solution comprising crude compound I" can be used interchangeably, both referring to a solution which contains the target compound I and one or more non-target compounds. The solution can be obtained by dissolving the crude compound I in water or a buffer solution, or a reaction solution comprising the compound of Formula I obtained from any process. The reaction solution comprising compound I from any process known in the art for preparing compound I can be used (see Example 1 of CN1040541C). For example (but not limited to), the solution is obtained by adding an amount of water or organic solvent into the transformation solution of compound I. The concentration of the organic solvent in the solution of crude compound I is 0%-2%.

As used herein, "loading" refers to the process of bringing the solution containing crude compound I into contact with a macroporous adsorption resin so that the crude compound I is adsorbed onto the macroporous adsorption resin. "Contact" includes directly feeding the macroporous adsorption resin into the solution and then agitating to allow the adsorption to occur; or filling the macroporous adsorption resin into a chromatographic device and the solution being allowed to flow through the chromatographic column.

"Washing" the macroporous adsorption resin means that a suitable buffer solution is allowed to pass through or over the macroporous adsorption resin.

As used herein, a "washing buffer solution" refers to a buffer solution used to wash the macroporous adsorption resin (mainly for removing the organic phase) before the target compound I is eluted. Conveniently, the washing buffer solution and the sample-loading buffer solution may, but not necessarily, be of the same polarity.

"Eluting" molecules from the macroporous adsorption resin means that the molecules are removed from the macroporous adsorption resin by changing the polarity of the buffer solution around the macroporous adsorption resin. Due to the polarity, the buffer solution can compete with the molecules for the adsorption sites on the macroporous adsorption resin.

As used herein, an "elution buffer solution" is used to elute the target compound I from a stationary phase. The target compound I can be eluted from the macroporous adsorption resin by the elution buffer solution.

"Purifying" the compound I from a composition comprising the target compound I and one or more non-target compounds means that the purity of compound I in the composition is increased by removing (totally or partially) at least one non-target compound from the composition.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The main advantages of the invention include:

1. A novel low-cost process for purifying cyclolipopeptide compound, particularly echinocandin compounds is provided;

2. The advantages of purifying steps in the process provided by the invention, such as, simple route, mild conditions, high purification yields, small amount of the used organic solvent, simple treatments, low pollution to the environment, and the like, to a great extent, reduce the requirements on process manipulation and equipments, thereby reducing the cost;

3. Stable target products can be obtained through the process provided by the invention, thereby facilitating the quality control on final products and large-scale production.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

In the following examples, the compound I is detected by HPLC:

Analysis is performed on Waters analytic HPLC system. Reverse-phase HPLC analysis is used for determining FR179642, echinocandin B and other analogues. The material and conditions used in the reverse-phase analysis are listed as follows: PLATISIL ODS chromatographic column (particle size 5 μm, 4.6 mm i.d×250 mm); temperature: 30° C.; mobile phase: 3% acetonitrile/0.5% sodium dihydrogen phosphate; flow rate: 1 ml/min; detected under 210 nm UV.

Example 1

Preparation of the Crude Compound 1 of Formula I

The reaction solution containing compound I was obtained according to Example 1 of U.S. Pat. No. 5,376,634. In the solution, the content of the compound I was 7.3 g/L, and the HPLC purity of the compound was 73.91% (see FIG. 1 and Table 1 for HPLC pattern).

TABLE 1

|  | Retention time | Area | Height | % Area |
|---|---|---|---|---|
| 1 | 5.257 | 52004 | 4607 | 1.15 |
| 2 | 5.815 | 202507 | 25208 | 4.49 |
| 3 | 6.432 | 87928 | 6165 | 1.95 |
| 4 | 6.895 | 8923 | 1043 | 0.20 |
| 5 | 7.291 | 121333 | 10471 | 2.69 |
| 6 | 7.710 | 44199 | 2234 | 0.98 |
| 7 | 8.353 | 11225 | 1099 | 0.25 |
| 8 | 9.578 | 3334358 | 165845 | 73.91 |
| 9 | 11.460 | 134324 | 9884 | 2.98 |
| 10 | 13.681 | 11436 | 779 | 0.25 |
| 11 | 14.848 | 9766 | 729 | 0.22 |
| 12 | 15.163 | 23807 | 1379 | 0.53 |
| 13 | 19.268 | 307011 | 6129 | 6.81 |
| 14 | 24.014 | 162338 | 6277 | 3.60 |

Example 2

Purification of Compound I 500 mL of solution containing crude compound I obtained in Example 1 was used in this Example, wherein the solution contained 3.65 g of compound I.

25 g of NaCl was added into the crude solution. Upon dissolution, the crude solution was loaded on a chromatographic column filled with 370 ml of HP20ss resin, wherein the flow rate for loading was 1 column volume per hour. Afterwards, 3% aqueous NaCl (2× column volumes) was used to wash the column with the flow rate for washing being 1 column volume per hour. And then, 1000 ml of pure water was used as the eluent, wherein the flow rate for eluting is 1 column volume per hour. Portions containing compound I were collected and mixed. The content of compound I in the eluate was determined as 3.4 g by HPLC (yield 93.2%), and its purity was 97.2%.

Example 3

Purification of Compound I

1 L solution containing crude compound I obtained in Example 1 was used in this Example, wherein the solution contained 7.3 g of compound I.

40 g of KCl was added into the crude solution. Upon dissolution, the crude solution was loaded on a chromatographic column filled with 0.8 L XAD-16 resin, wherein the flow rate for loading was 1 column volume per hour. Afterwards, pure water (5× column volumes) was used to wash the column with the flow rate for washing being 1 column volume per hour. And then, 2.5 L of 3% aqueous methanol was used as the eluent, wherein the flow rate for eluting is 1 column volume per hour. Portions containing compound I were collected and mixed. The content of compound I in the eluate was determined as 6.6 g by HPLC (yield 90.4%), and its purity was 96.5%.

Example 4

Purification of Compound I

1 L solution containing crude compound I obtained in Example 1 was used in this Example, wherein the solution contained 7.3 g of compound I.

The crude solution was added into a plastic dosing-cup (5 L). Into the dosing-cup, 1.4 L XAD-16HP resin and 50 g of $(NH_4)_2SO_4$ were added. The resulting mixture was agitated for 120 mins at the room temperature, and then filtered by a Büchner funnel on which a piece of filter paper was laid. The filtrate was discarded, and the resin was loaded on a chromatographic column. 3 L of pure water was used to wash the column. Afterwards, 5 L of 4% aqueous acetone was used as the eluent. Portions containing compound I were collected.

The content of compound I in the eluate was determined as 6.7 g by HPLC (yield 92.5%), and its purity was 97.3%.

Example 5

Purification of Compound I 0.5 L solution containing crude compound I obtained in Example 1 was used in this Example, wherein the solution contained 4.6 g of compound I.

Figure 2:
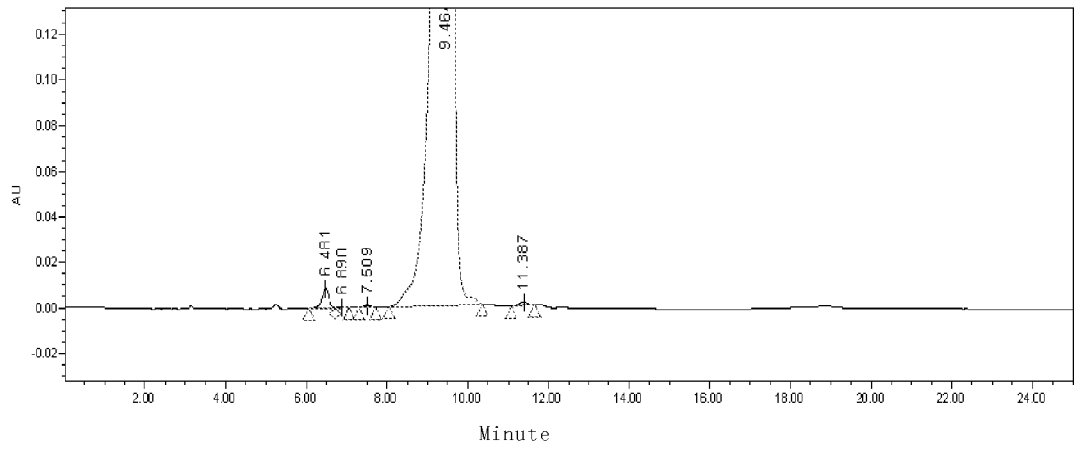
FIG. 2 shows the HPLC chromatogram of the compound of Formula I purified in Example 6.

The crude solution was loaded on a chromatographic column filled with 300 ml SP207ss resin, wherein the flow rate for loading was 5 column volumes per hour. Afterwards, 1% aqueous ethanol (2× column volumes) was used to wash the column with the flow rate for washing being 1 column volume per hour, and 2% aqueous ethanol (2× column volumes) was used to wash the column with the flow rate for washing being 1 column volume per hour. And then, 3.6 L of 3% aqueous ethanol was used as the eluent, wherein the flow rate for eluting is 1 column volume per hour. Portions containing compound I were collected and mixed. The content of compound I in the eluate was determined as 4.33 g by HPLC (yield 94.2%), and its purity was 99.0% (see FIG. 2 and Table 2 for HPLC pattern).

TABLE 2

|   | Retention time | Area | Height | % Area |
|---|---|---|---|---|
| 1 | 6.481 | 100952 | 8789 | 0.41 |
| 2 | 6.890 | 29266 | 406 | 0.12 |
| 3 | 7.509 | 34144 | 889 | 0.14 |
| 4 | 9.464 | 24141515 | 1222680 | 99.00 |
| 5 | 11.387 | 82921 | 1983 | 0.33 |

Example 6

Purification of Compound I 0.5 L of solution containing crude compound I obtained in Example 1 was used in this Example, wherein the solution contained 4.6 g of compound I.

The crude solution was loaded on a chromatographic column filled with 600 ml of SP207ss resin, wherein the flow rate for loading was 5 column volumes per hour. Afterwards, pure water (2× column volumes) was used to wash the column with the flow rate for washing being 1 column volume per hour. And then, 7.2 L of 2% aqueous ethanol was used as the eluent, wherein the flow rate for eluting is 2 column volumes per hour. Portions containing compound I were collected and mixed. The content of compound I in the eluate was determined as 4.4 g by HPLC (yield 95.6%), and its purity was 99.0%.

Example 7

Purification of Compound I 0.5 L of solution containing crude compound I obtained in Example 1 was used in this Example, wherein the solution contained 4.6 g of compound I.

The crude solution was loaded on a chromatographic column filled with 46 L of SP207 resin, wherein the flow rate for loading was 5 column volumes per hour. Afterwards, pure water (2× column volumes) was used to wash the column with the flow rate for washing being 1 column volume per hour. And then, 150 L of 20% aqueous ethanol was used as the eluent, wherein the flow rate for eluting is 2 column volumes per hour. Portions containing compound I were collected and mixed. The content of compound I in the eluate was determined as 4.02 g by HPLC (yield 87.4%), and its purity was 98.1%.

Example 8

Purification of Compound I 0.5 L of solution containing crude compound I obtained in Example 1 was used in this Example, wherein the solution contained 4.6 g of compound I.

The crude solution was loaded on a chromatographic column filled with 460 ml of SP207 resin, wherein the flow rate for loading was 5 column volumes per hour. Afterwards, 1% aqueous ethanol (2× column volumes) was used to wash the column with the flow rate for washing being 1 column volume per hour. And then, 3.0 L of 5% aqueous ethanol was used as the eluent, wherein the flow rate for eluting is 1 column volumes per hour. Portions containing compound I were collected and mixed. The content of compound I in the eluate was determined as 4.4 g by HPLC (yield 95.6%), and its purity was 97.9%.

Comparative Example 1

Purification of Compound I 500 mL of solution containing crude compound I obtained in Example 1 was used in this Example, wherein the solution contained 3.65 g of compound I.

The crude solution was loaded on a chromatographic column filled with 370 ml of HP20ss resin, wherein the flow rate for loading was 1 column volumes per hour. Afterwards, 1000 mL of pure water was used as the eluent, wherein the flow rate for eluting is 1 column volumes per hour. Portions containing compound I were collected and mixed. The content of compound I in the eluate was determined as 3.4 g by HPLC (yield 93.2%), and its purity was 75.2%.

Comparative Example 2

1 L of solution containing crude compound I obtained in Example 1 was used in this Example, wherein the solution contained 7.3 g of compound I.

The crude solution was loaded on a chromatographic column filled with 0.8 L of XAD-16 resin, wherein the flow rate for loading was 1 column volumes per hour. Afterwards, pure water (5× column volumes) was used to wash the column with the flow rate for washing being 1 column volume per hour. And then, 2.5 L of 3% aqueous methanol was used as the eluent, wherein the flow rate for eluting is 1 column volumes per hour. Portions containing compound I were collected and mixed. The content of compound I in the eluate was determined as 6.6 g by HPLC (yield 50.4%), and its purity was 79.5%.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:

1. A method of purifying the compound of Formula I

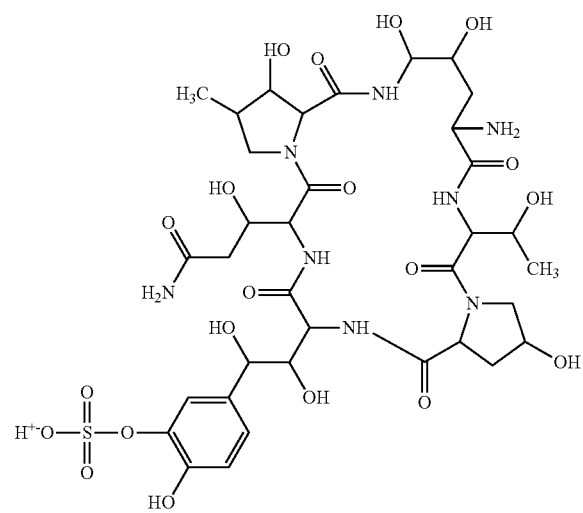

or the salts thereof, said method comprising:
loading the crude compound of Formula I onto a macroporous adsorption resin;
washing the macroporous adsorption resin using water, an organic solvent or a mixed solution of an organic solvent and water as the washing liquid, wherein said organic solvent comprises a C1-C4 alcohol or a C1-C4 ketone; and
eluting the compound of Formula I from the macroporous adsorption resin using water, an organic solvent or a mixed solution of an organic solvent and water as the eluent.

2. The purification process according to claim 1, wherein said loading comprises allowing a solution comprising the crude compound of Formula I to flow through a chromatographic column filled with the macroporous adsorption resin or mixing a solution comprising the crude compound of Formula I with the macroporous adsorption resin.

3. The purification process according to claim 2, wherein said loading comprises allowing a solution comprising the crude compound of Formula I to flow through a chromatographic column filled with the macroporous adsorption resin.

4. The purification process of claim 1, wherein the macroporous adsorption resin is selected from a non-polar aromatic adsorption resin polymerized from styrene and divinylbenzene, or a methacrylic adsorption resin of moderate polarity with methacrylate units in its structure.

5. The purification process according to claim 4, wherein the macroporous adsorption resin is selected from the group consisting of XAD-16, XAD-16HP, HP-20ss, SP-207, SP207ss, or the mixture thereof.

6. The purification process according to claim 4, wherein the adsorption resin comprises halogen and is bonded with styrene polymer matrix through chemistry bond.

7. The purification process according to claim 6, wherein the adsorption resin comprises bromine and is bonded with styrene polymer matrix through chemistry bond.

8. The purification process according to claim 7, wherein the adsorption resin is selected from: SP-207, SP-207ss, or a mixture thereof.

9. The purification process according to claim 2, wherein the solution comprising the crude compound of Formula I comprises ionizable salts, and the macroporous adsorption resin is selected from a non-polar aromatic adsorption resin polymerized from styrene and divinylbenzene.

10. The purification process according to claim 9, wherein the ionizable salt is selected from the group consisting of sulfates, nitrates, salts comprising halogen, phosphates, acetates, carbonates, citrates, silicates, persulfates, chromates, lactates, oxalates, and mixtures thereof.

11. The purification process according to claim 1, wherein the organic solvent is selected from the group consisting of methanol, ethanol, propanol, butanol, acetone, butanone, and mixtures thereof.

12. The purification process of claim 1, wherein in said washing, the volume percentage of the organic solvent is 0-3% based on the total volume of the washing liquid.

13. The purification process of claim 1, wherein in said eluting, the volume percentage of the organic solvent is 0-20% based on the total volume of the eluent.

14. The purification process of claim 1, wherein in said loading, the weight ratio of the crude compound of Formula I to the macroporous adsorption resin is 0.1-15 (g/L).

15. The purification process of claim 3, wherein said solution is allowed to flow at a flow rate ranging from 0.1 to 10 column volumes per hour.

16. The purification process of claim 1, wherein in said washing, the volume percentage of the organic solvent is 0-2%, based on the total volume of the washing liquid.

17. The purification process of claim 1, wherein in said eluting, the volume percentage of the organic solvent is 0-5%, based on the total volume of the eluent.

* * * * *